United States Patent
Friend

(10) Patent No.: US 9,541,420 B2
(45) Date of Patent: Jan. 10, 2017

(54) SYSTEM FOR DETERMINING ERROR IN A SENSED MACHINE POSITION

(71) Applicant: Caterpillar Inc., Peoria, IL (US)

(72) Inventor: Paul Friend, Morton, IL (US)

(73) Assignee: Caterpillar Inc., Peoria, IL (US)

( * ) Notice: Subject to any disclaimer, the term of this patent is extended or adjusted under 35 U.S.C. 154(b) by 870 days.

(21) Appl. No.: 13/856,037

(22) Filed: Apr. 3, 2013

(65) Prior Publication Data

US 2014/0303923 A1    Oct. 9, 2014

(51) Int. Cl.

| | |
|---|---|
| *G01C 17/38* | (2006.01) |
| *G01C 25/00* | (2006.01) |
| *G01C 19/00* | (2013.01) |
| *G01D 18/00* | (2006.01) |
| *G01D 21/00* | (2006.01) |
| *G01P 21/00* | (2006.01) |
| *G01R 35/00* | (2006.01) |
| *G01C 21/16* | (2006.01) |
| *G01D 3/02* | (2006.01) |
| *G01S 7/497* | (2006.01) |
| *G01D 5/244* | (2006.01) |
| *G01N 21/27* | (2006.01) |

(52) U.S. Cl.
CPC .......... *G01C 25/005* (2013.01); *G01C 21/165* (2013.01); *G01D 3/022* (2013.01); *G01D 5/2448* (2013.01); *G01N 21/274* (2013.01); *G01S 7/497* (2013.01)

(58) Field of Classification Search
CPC ...... G01N 21/274; H03M 1/00; G01B 21/042; G01B 21/045; G01P 21/02
See application file for complete search history.

(56) References Cited

U.S. PATENT DOCUMENTS

| | | | | |
|---|---|---|---|---|
| 5,319,374 A | * | 6/1994 | Desai .................... | G01S 19/23 342/357.43 |
| 5,394,333 A | | 2/1995 | Kao | |
| 5,517,419 A | * | 5/1996 | Lanckton .............. | G01C 11/02 348/148 |
| 5,877,723 A | * | 3/1999 | Fan ....................... | G01S 19/53 342/357.31 |
| 5,906,655 A | * | 5/1999 | Fan ....................... | G01C 21/165 342/457 |
| 5,913,915 A | * | 6/1999 | McQuinn ............. | A01B 79/005 700/231 |

(Continued)

FOREIGN PATENT DOCUMENTS

| | | | | | |
|---|---|---|---|---|---|
| JP | | 2000026096 A | * | 1/2000 | |
| WO | WO | 2012151333 A2 | * | 11/2012 | .............. G06T 7/20 |

*Primary Examiner* — Mohamed Charioui
*Assistant Examiner* — Leonard S Liang
(74) *Attorney, Agent, or Firm* — Leydig, Voit & Mayer, Ltd.; L. Glenn Waterfield

(57) ABSTRACT

A system for determining an error in a sensed position of a machine includes a position sensing system, a dead reckoning system, and a controller. The controller is configured to determine a difference between a sensed position and a calculated position determined by dead reckoning. The difference is compared to an error threshold defining a maximum acceptable distance between the sensed position of the machine and the calculated position of the machine and an error signal generated if the difference exceeds the error threshold. A pair of offset dead reckoning processes may be used.

15 Claims, 4 Drawing Sheets

(56) References Cited

U.S. PATENT DOCUMENTS

| | | | | |
|---|---|---|---|---|
| 5,991,692 | A * | 11/1999 | Spencer, II | G01P 13/00 701/468 |
| 6,029,111 | A * | 2/2000 | Croyle | G01C 21/165 701/468 |
| 6,089,743 | A * | 7/2000 | McQuinn | A01B 79/005 111/130 |
| 6,445,983 | B1 * | 9/2002 | Dickson | A01B 69/008 701/23 |
| 6,453,223 | B1 * | 9/2002 | Kelly | G05D 1/0246 318/587 |
| 6,496,778 | B1 | 12/2002 | Lin | |
| 6,510,367 | B1 * | 1/2003 | McQuinn | A01B 79/005 111/130 |
| 6,577,952 | B2 | 6/2003 | Geier et al. | |
| 7,177,737 | B2 | 2/2007 | Karlsson et al. | |
| 7,756,639 | B2 | 7/2010 | Colley et al. | |
| 7,899,599 | B2 | 3/2011 | Mäkelä et al. | |
| 8,378,887 | B2 | 2/2013 | Xie et al. | |
| 8,560,218 | B1 * | 10/2013 | Kahn | G01S 19/215 701/469 |
| 8,812,233 | B2 * | 8/2014 | Kontz | 701/502 |
| 2003/0036847 | A1 | 2/2003 | Geier et al. | |
| 2005/0049787 | A1 * | 3/2005 | Cho, II | G01S 19/49 701/472 |
| 2005/0065722 | A1 * | 3/2005 | Wood | G01C 21/12 701/468 |
| 2005/0065726 | A1 * | 3/2005 | Meyer | B61L 25/021 701/470 |
| 2008/0294342 | A1 * | 11/2008 | Hoshizaki | G01C 21/165 701/472 |
| 2009/0018772 | A1 * | 1/2009 | Watanabe | G01C 21/165 701/472 |
| 2011/0243454 | A1 * | 10/2011 | Miyajima | G01C 21/28 382/195 |
| 2012/0136524 | A1 * | 5/2012 | Everett | E02F 9/2045 701/24 |
| 2012/0173185 | A1 * | 7/2012 | Taylor | G01B 11/026 702/104 |
| 2012/0299702 | A1 * | 11/2012 | Edara | G01S 19/49 340/8.1 |
| 2013/0160543 | A1 * | 6/2013 | Kontz | G01C 19/5776 73/504.12 |
| 2013/0297204 | A1 * | 11/2013 | Bartels | G01C 21/165 701/495 |
| 2013/0346127 | A1 * | 12/2013 | Jensen | G06Q 10/06 705/7.12 |
| 2014/0180579 | A1 * | 6/2014 | Friend | G01B 11/00 701/469 |
| 2014/0222247 | A1 * | 8/2014 | Friend | G05D 1/0276 701/2 |

* cited by examiner

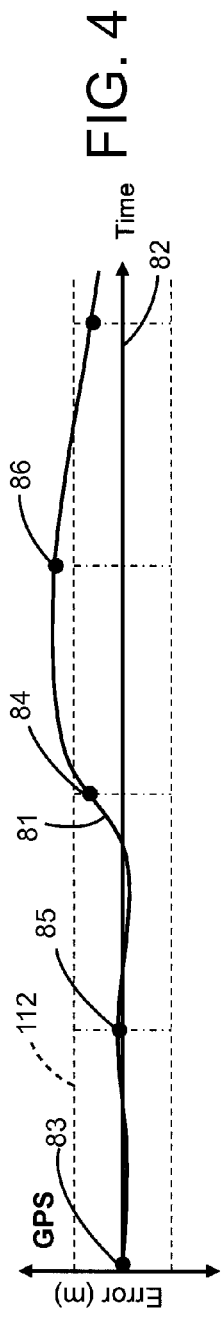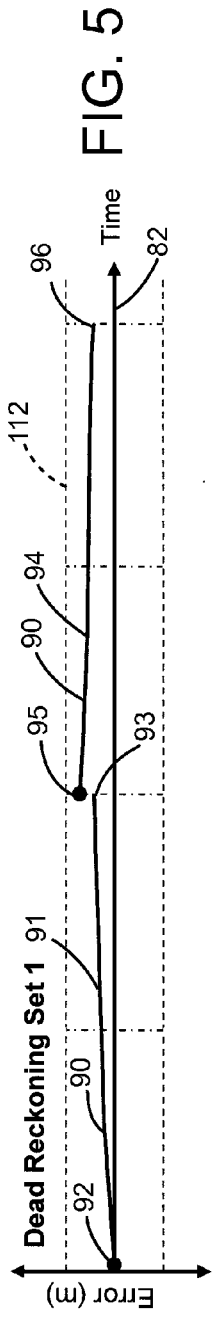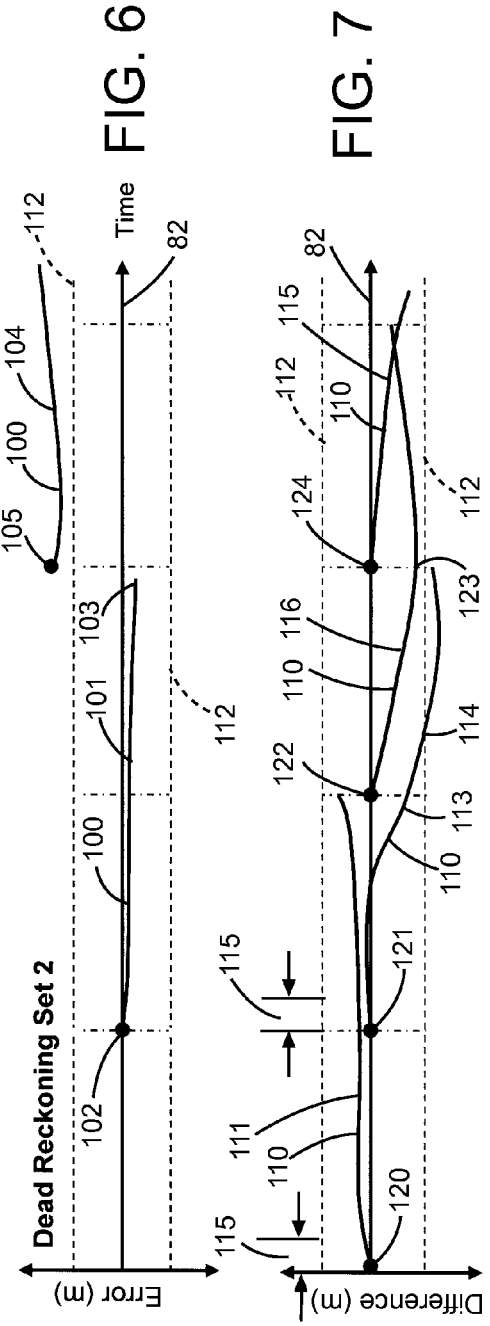

SYSTEM FOR DETERMINING ERROR IN A SENSED MACHINE POSITION

TECHNICAL FIELD

This disclosure relates generally to controlling movement of a machine and, more particularly, to a system and method for confirming the accuracy of a sensed position of the machine.

BACKGROUND

Machines such as dozers, load trucks, motor graders, wheel loaders, etc., are used to perform a variety of tasks at a work site such as moving material and performing other operations. The machines may operate in an autonomous, semi-autonomous, or manual manner to perform these tasks in response to commands generated as part of a work plan for the machines. Autonomously and semi-autonomously operated machines may increase productivity and permit operation in environments that are unsuitable or undesirable for a human operator. Autonomous or semi-autonomous systems may also compensate for inexperienced human operators as well as inefficiencies associated with repetitive tasks.

As a machine performs its tasks, it may receive information and instructions from systems that are located remotely from the machine. In one example, the machine may include a position sensing system having sensors that receive signals from a global navigation satellite system or a global positioning system (collectively referred to as "GPS"). The signals from the GPS may be used to determine the position of the machine. To increase the accuracy of the position sensing system, some machines further include additional systems that work with the GPS. For example, some machines use data from an inertial measurement unit ("IMU") to supplement the position generated by the GPS. In doing so, the machine may use the IMU data to estimate the position of the machine during the interval between the receipt of GPS signals.

When relying upon GPS signals to establish the position of a machine being operated autonomously or semi-autonomously, early detection of errors in the position sensing system may be desirable. However, certain types of errors in GPS signals such as those caused by multi-path effects, system noise, propagation delays, and other influences may be difficult to detect. This may be particularly true for errors that occur relatively slowly. For example, a newly detected position that would indicate a large change in position may be readily dismissed if a machine is moving relatively slowly. However, determining the accuracy of relatively small changes in position may be more difficult.

U.S. Pat. No. 6,496,778 discloses a positioning system with an inertial measurement unit and a global positioning system processor. The system combines inertial measurement output with global positioning signals to improve the performance of the inertial measurement unit. Output from the inertial measurement unit may subsequently be used in conjunction with the global positioning system to improve the output from the global positioning system.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

A system for determining an error in a sensed position of a machine includes a position sensing system associated with the machine for determining a sensed position of the machine, a dead reckoning system associated with the machine for determining a calculated position of the machine, and a controller. The controller is configured to store an error threshold defining a maximum acceptable distance between the sensed position of the machine and the calculated position of the machine, determine an initialization position based upon the position sensing system, and determine a calculated position based upon the initialization position and the dead reckoning system. The controller is further configured to determine a sensed position based upon the position sensing system, determine a difference between the calculated position and the sensed position, compare the difference to the error threshold, and generate an error signal if the difference exceeds the error threshold.

In another aspect, a controller-implemented method for determining an error in a sensed position of a machine includes storing an error threshold defining a maximum acceptable distance between a sensed position of the machine based upon a position sensing system and a calculated position of the machine based upon a dead reckoning system, determining an initialization position based upon the position sensing system, and determining a calculated position based upon the initialization position and the dead reckoning system. The method further includes determining a sensed position based upon the position sensing system, determining a difference between the calculated position and the sensed position, comparing the difference to the error threshold, and generating an error signal if the difference exceeds the error threshold.

In still another aspect, an autonomously operated machine includes a propulsion system, a steering system, a position sensing system associated with the machine for determining a sensed position of the machine, a dead reckoning system associated with the machine for determining a calculated position of the machine, an accuracy verification system for determining an error in the sensed position, and a controller. The controller is configured to store an error threshold defining a maximum acceptable distance between the sensed position of the machine and the calculated position of the machine, determine an initialization position based upon the position sensing system, and determine a calculated position based upon the initialization position and the dead reckoning system. The controller is further configured to determine a sensed position based upon the position sensing system, determine a difference between the calculated position and the sensed position, compare the difference to the error threshold, and generate an error signal if the difference exceeds the error threshold.

BRIEF DESCRIPTION OF THE DRAWINGS

FIG. 4 is an exemplary performance graph of the error in the sensed machine position as a function of time;

FIG. 5 is an exemplary performance graph of a first set of dead reckoning cycles based upon initialization positions from FIG. 4;

FIG. 6 is an exemplary performance graph of a second set of dead reckoning cycles based upon initialization positions from FIG. 4; and FIG. 7 is an exemplary performance graph of sensed position verification cycles based upon the difference between the sensed machine position of FIG. 4 and the dead reckoning cycles of FIGS. 5-6.

DETAILED DESCRIPTION

Figure 1:
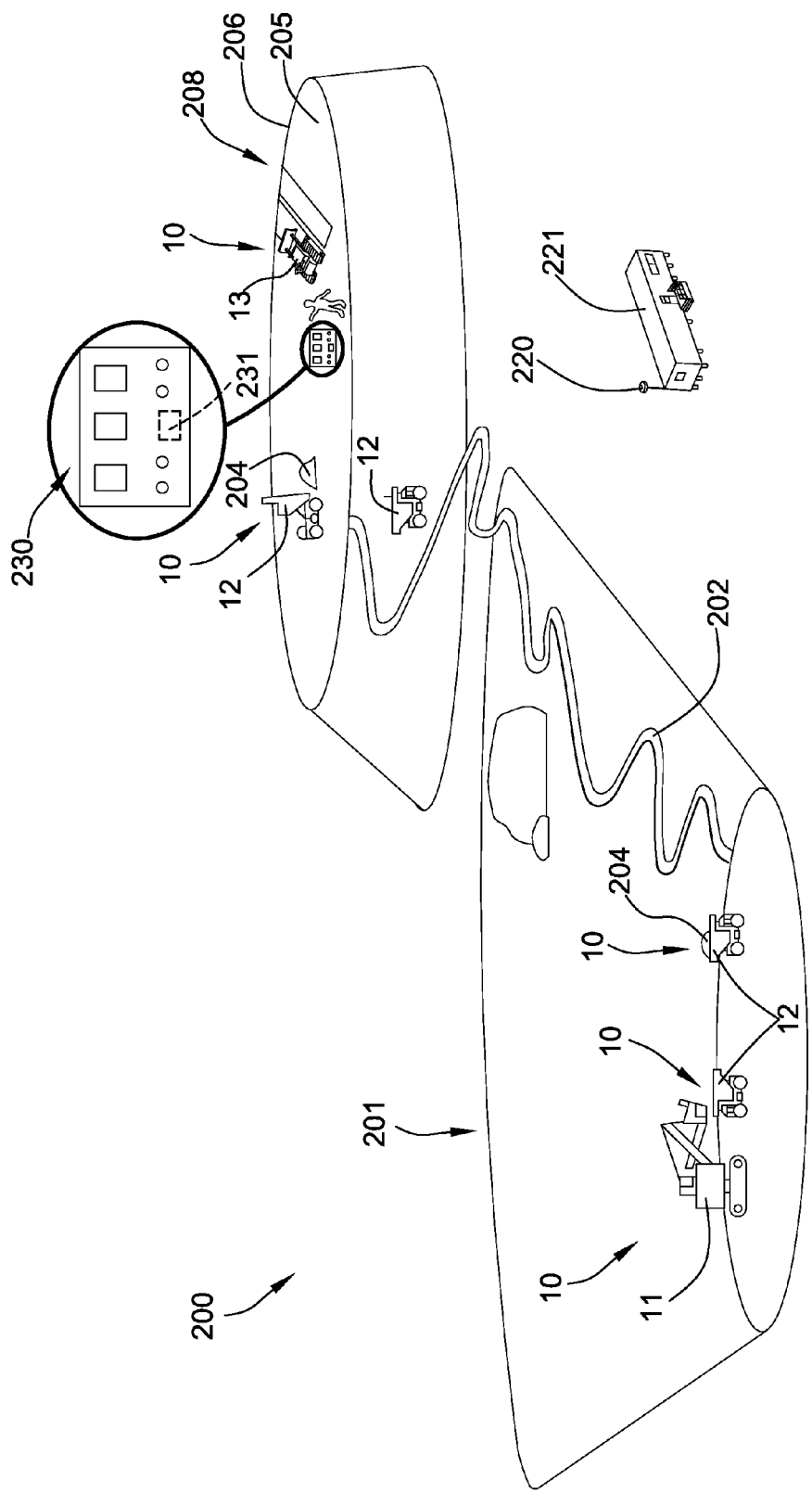
FIG. 1 shows a schematic view of a work site at which a machine incorporating the principles disclosed herein may be used.

FIG. 1 depicts a diagrammatic illustration of a work site 200 at which one or more machines 10 may operate in an autonomous, a semi-autonomous, or manual manner. Work site 200 may be a portion of a mining site, a landfill, a quarry, a construction site, a roadwork site, a forest, a farm, or any other area in which movement of machines is desired. As depicted, work site 200 includes an open-cast or open pit mine 201 from which material 204 may be excavated or removed by a machine such as an excavator 11 and loaded into a machine such as a load truck 12. The load trucks 12 may travel along a road 202 to dump location 208 at which the material 204 is dumped. A machine such as a dozer 13 may move material 204 along the work surface 205 towards a crest 206 such as an edge of a ridge, embankment, high wall or other change in elevation.

As used herein, a machine 10 operating in an autonomous manner operates automatically based upon information received from various sensors without the need for human operator input. As an example, a haul or load truck that automatically follows a path from one location to another and dumps a load at an end point may be operating autonomously. A machine 10 operating semi-autonomously includes an operator, either within the machine or remotely, who performs some tasks or provides some input and other tasks are performed automatically and may be based upon information received from various sensors. As an example, a load truck 12 that automatically follows a path from one location to another but relies upon an operator command to dump a load may be operating semi-autonomously. In another example of a semi-autonomous operation, an operator may dump a bucket from an excavator 11 in a load truck 12 and a controller may automatically return the bucket to a position to perform another digging operation. A machine 10 being operated manually is one in which an operator is controlling all or essentially all of the functions of the machine. A machine 10 may be operated remotely by an operator (i.e., remote control) in either a manual or semi-autonomous manner.

Figure 2:
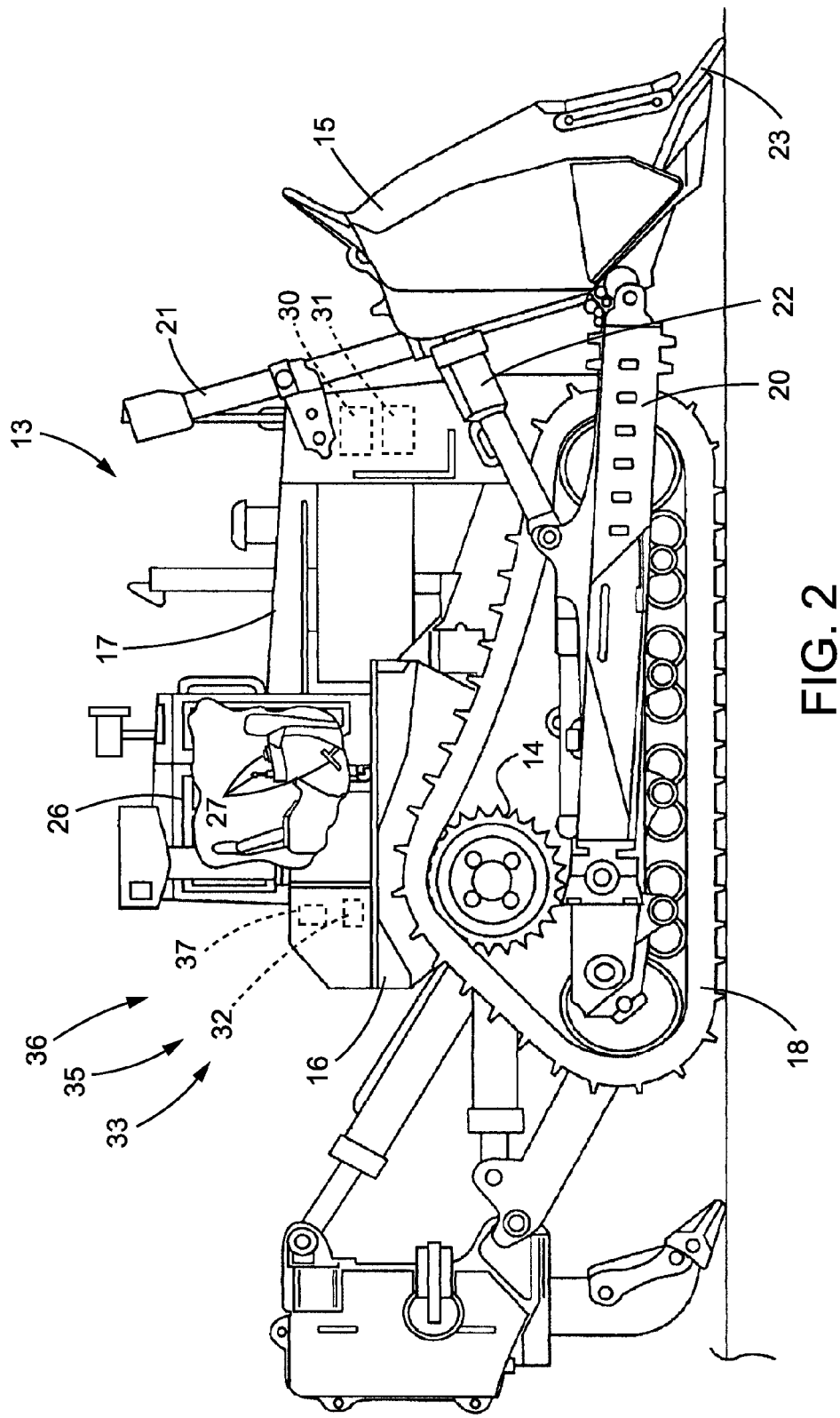
FIG. 2 shows a diagrammatic illustration of a machine in accordance with the disclosure.

FIG. 2 shows a diagrammatic illustration of a machine 10 such as a dozer 13 with a work implement or a blade 15 for moving material 204. The machine 10 includes a frame 16 and a prime mover such as an engine 17. A ground-engaging drive mechanism such as a track 18 is driven by a drive wheel 19 on each side of machine 10 to propel the machine. Although machine 10 is shown in a "track-type" configuration, other configurations, such as a wheeled configuration, may be used. Operation of the engine 17 and a transmission (not shown) which are operatively connected to the tracks 18 and drive wheels 19 may be controlled by a control system 35 including a controller 36. Other types of propulsion systems for causing movement of the machine 10 are contemplated.

Machine 10 may include a ground engaging work implement such as blade 15 pivotally connected to frame 16 by arms 20 on each side of machine 10. First hydraulic cylinder 21 coupled to frame 16 supports blade 15 in the vertical direction, and allows blade 15 to move up or down vertically from the point of view of FIG. 2. Second hydraulic cylinders 22 on each side of machine 10 allow the pitch angle of blade tip 23 to change relative to a centerline of the machine.

Machine 10 may include a cab 26 that an operator may physically occupy and provide input to control the machine. Cab 26 may include one or more input devices 27 through which the operator issues commands to control the propulsion system and steering system of the machine as well as operate various implements associated with the machine.

Machine 10 may be equipped with a plurality of sensors that provide data indicative (directly or indirectly) of various operating parameters of the machine. The term "sensor" is meant to be used in its broadest sense to include one or more sensors and related components that may be associated with the machine 10 and that may cooperate to sense various functions, operations, and operating characteristics of the machine.

One or more movement sensors may be positioned on the machine 10 for sensing movement of the machine 10 and generating movement signals indicative of movement of the machine. A pitch rate sensor 30 (e.g., a gyroscope may be provided or mounted on the machine 10, on the blade 15, or on an implement frame member to which the blade is mounted. The pitch rate sensor 30 may be used to provide a pitch rate signal indicative of a measured pitch rate of the machine 10 or the blade 15 depending on where the sensor is mounted. The pitch rate sensor 30 may be a "stand-alone" sensor or part of a multi-function sensor such as an inertial measurement unit that also measures the acceleration of the machine 10 along various axes. The pitch rate measured by the pitch rate sensor 30 is indicative of the rate of change of the pitch angle of the sensor.

An acceleration sensor 31 (e.g., a 3-axis accelerometer) may be provided as a separate component or as part of a multi-function sensor such as an inertial measurement unit. The acceleration sensor 31 may be used to provide an acceleration signal indicative of acceleration of the machine 10 relative to a gravity reference. If the acceleration sensor 31 is not part of a multi-function sensor, it may be positioned adjacent the pitch rate sensor 30 or at another location on machine 10.

Other types of movement measurement sensors such as sensors for measuring, directly or indirectly, the speed of the machine 10 are also contemplated.

A position sensing system 32, as shown generally by an arrow in FIG. 2 indicating association with the machine 10, may include a position sensor 33 to sense a position of the machine relative to the work site 200. The position sensor 33 may include a plurality of individual sensors that cooperate to provide position signals to controller 36 to indicate the position of the machine 10. In one example, the position sensor 33 may include one or more sensors that interact with a positioning system such as a GPS to operate as a GPS sensor. The controller 36 may determine the position of the machine 10 within work site 200 as well as the orientation of the machine such as its heading, pitch and roll. In other examples, the position sensor 33 may be another type of sensor or system that determines the position of machine 10.

In some instances, the position sensing system 32 may also operate in conjunction with the movement measuring sensors (e.g., pitch rate sensor 30 and/or acceleration sensor 31) of the machine 10 to increase the accuracy of the position sensing system. The position sensing system 32 may use data from the movement measuring sensors to supplement the position as determined from the position signals alone. For example, the movement measuring sensors may generate signals more frequently than the position sensor 33 (e.g., every 10 milliseconds versus every 100 milliseconds). The position sensing system 32 may use the movement signals from the movement measuring sensors to determine the current position of the machine 10 based upon dead reckoning between the receipt of the signals from the position sensor 33. In doing so, the position sensing system 32 may integrate the signals from the movement measuring system and combine the resulting calculated movement with the last-known position based upon signals from the position sensing system 32. Such process may also be useful in instances in which the signals of the position sensing system 32 are interrupted such as due to noise or breaks in the transmission link.

Machine 10 may be controlled by a control system 35 as shown generally by an arrow in FIG. 2 indicating association with the machine 10. The control system 35 may include an electronic control module or controller 36. The controller 36 may receive input command signals from a wireless network system 220 (FIG. 1), remote control input command signals from an operator using a remote control unit or remote control console 230 to operate machine 10 remotely, or operator input command signals from an operator operating the machine 10 from within cab 26. The controller 36 may control the operation of various aspects of the machine 10 including the drivetrain as well as the hydraulic systems and other systems that operate the blade 15. The control system 35 may utilize various input devices to control the machine 10 and one or more sensors to provide data and input signals representative of various operating parameters of the machine 10 and the environment of the work site 200.

The controller 36 may be an electronic controller that operates in a logical fashion to perform operations, execute control algorithms, store and retrieve data and other desired operations. The controller 36 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller 36 such as power supply circuitry, signal conditioning circuitry, driver circuitry, and other types of circuitry.

The controller 36 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 36 may be implemented in hardware and/or software without regard to the functionality. The controller 36 may rely on one or more data maps relating to the operating conditions and the operating environment of the machine 10 and the work site 200 that may be stored in the memory of controller. Each of these data maps may include a collection of data in the form of tables, graphs, and/or equations.

The control system 35 may be located on the machine 10 and may also include components located remotely from the machine such as at a command center 221 (FIG. 1) or at the remote control console 230. The functionality of control system 35 may be distributed so that certain functions are performed at machine 10 and other functions are performed remotely. Machine 10 may be configured to be operated autonomously, semi-autonomously, or manually. In case of semi-autonomous or manual operation, the machine may be operated by remote control and/or by an operator physically located within the cab 26. Still further, if the machine is being operated via remote control, a portion of the control system 35 may be located at the remote control unit or remote control console 230. Machine 10 may include a machine controller 37 and remote control console 230 may include a console controller 231. The machine controller 37 and the console controller 231 may be components of controller 36.

As stated above, the position sensing system 32 may use data from the movement measuring sensors to increase the accuracy of the position sensing system. The increased accuracy may be achieved by dead reckoning through the use of the data from the movement measuring sensors to generate additional position data during the intervals between the receipt of data from the position sensor 33. However, a dead reckoning process will not increase the accuracy of the position sensing system if the underlying position data from the position sensing system 32 is incorrect (i.e., the machine 10 is not actually at the location determined by the position sensing system 32). In other words, since the position sensing system 32 is starting with incorrect position data, dead reckoning from the last known position will merely build upon erroneous position data.

Accordingly, determining whether the position of the machine 10 actually matches the sensed position as determined by the position sensing system 32 is desirable. When a relatively fast change in sensed position occurs, the position sensing system 32 may indicate a large change in position from one signal to the next. In such case, the controller 36 may be able to determine that the indicated new position is erroneous based on the magnitude of the change and the operating conditions of machine 10, and take appropriate action such as, for example, ignore the new position, generate an alert command, slow the machine 10, and/or stop the machine. However, when a gradual error occurs, such error may not be readily detectable by the controller 36. Accordingly, controller 36 may include an accuracy verification system 38, as shown generally by an arrow in FIG. 2 indicating association with the machine 10, to confirm the accuracy or integrity of the sensed position of the machine 10 as determined by the position sensing system 32. If the accuracy verification system 38 determines that the sensed position of the machine 10, as determined by the position sensing system 32, is incorrect, the controller 36 may be configured to generate an error signal which may be used to reduce or stop the movement of the machine.

The accuracy verification system 38 may be configured to utilize the position sensing system 32 together with signals from the movement measuring sensors to check or determine the accuracy of the sensed position of the machine 10. In doing so, the accuracy verification system 38 may be configured to operate one or more repeating sets of dead reckoning cycles while the position sensing system 32 is receiving signals from position sensor 33. If more than one set of dead reckoning cycles is used, the cycles may be offset so that the cycles operate in a parallel but staggered or offset manner.

More specifically, the accuracy verification system 38 may be configured to periodically set a baseline or initialization position based upon the sensed position of the machine 10 as determined by the position sensing system 32. The time period between setting the initialization positions may be referred to as the error detection period. The signals from the movement measuring sensors may then be used with the initialization position as part of a verification cycle to calculate, by dead reckoning, a calculated or integrated position of the machine 10. The movement measuring sensors may thus be used as dead reckoning sensors and the signal or signals generated by the dead reckoning sensors may be referred to as dead reckoning signals. As such, the dead reckoning sensors may be all or any combination of the pitch rate sensor 30, the acceleration sensor 31, any sensors used to generate signals that may be used to determine the velocity of the machine 10, and any other desired sensors that may be used to sense movement of the machine. The calculated position and the sensed position may be compared and if the difference between the calculated position and the sensed position is greater than a predetermined amount or distance, referred to herein as the error threshold, the controller 36 may generate an error signal that may be used to issue an alert notification, reduce the speed of or stop the machine 10, and/or take any other desired action.

If desired, the accuracy verification system 38 may be configured to simultaneously operate with two or more repeating verification cycles having staggered initialization positions so that the accuracy verification system is always operating within one verification cycle even as a new verification cycle is starting. As a result, the accuracy verification system 38 always has at least one verification cycle in process.

Figure 3:
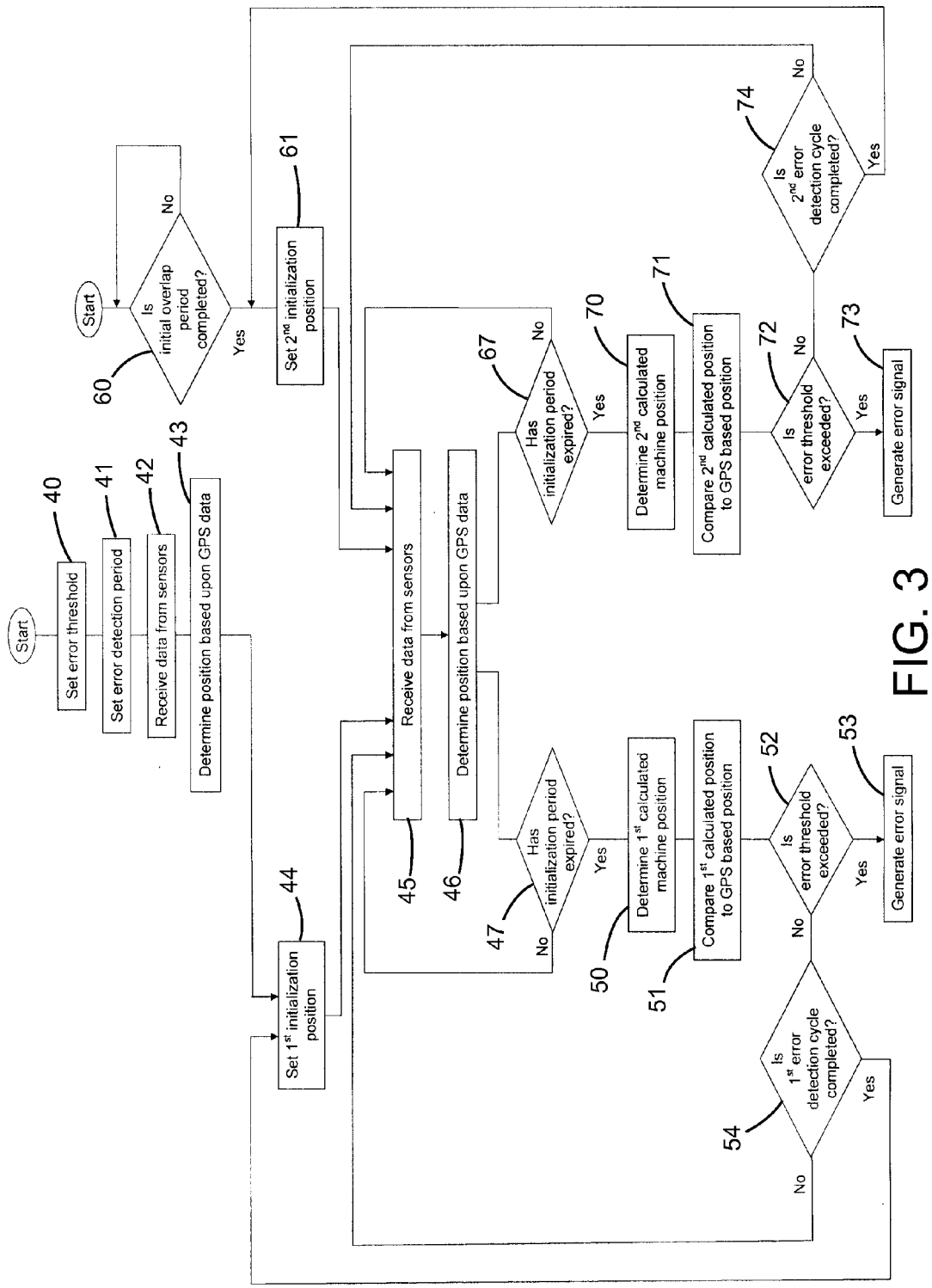
FIG. 3 shows a flowchart illustrating an accuracy verification system in accordance with the disclosure.

Referring to FIG. 3, the operation of an exemplary accuracy verification system 38 is depicted. At stage 40, the error threshold may be set or stored within the controller 36. The error threshold may define a maximum acceptable distance between a sensed position of the machine based in part upon the position signals from the position sensor 33 and the calculated position of the machine determined by the dead reckoning process. In other words, the error threshold defines the maximum acceptable distance between the sensed position as determined by the position sensing system 32 and the calculated position determined by a dead reckoning calculation as described in further detail below. The amount or distance of the error threshold may be set based upon any or all of the operations being performed, the location of the machine 10 within the work site 200, the operating conditions at the works site, and any other desired factors.

At stage 41, the error detection period may be set or stored within controller 36. The error detection period is the length of each dead reckoning or verification cycle performed by the accuracy verification system 38. Examples of dead reckoning cycles are depicted in FIGS. 5-6 as 90 and 100 and examples of verification cycles are depicted in FIG. 7 as 110. The length of the error detection cycle may be set based upon the accuracy of the dead reckoning or movement measurement sensors. In general, the greater the accuracy of the movement measurement sensors, the longer the error detection period may be. This is due to the increase in error in the calculated position when errors from the movement measurement sensors are integrated during the dead reckoning process. Solely for illustrative purposes, a relatively imprecise inertial measurement unit may permit an error detection period of approximately ten to twenty seconds while a more precise inertial measurement unit may permit an error detection period of approximately one hundred seconds. Other error detection periods may be used based upon characteristics of the movement measurement sensors and other characteristics of the accuracy verification system 38 as well as control system 35.

The controller 36 may receive at stage 42 data from the position sensor 33 and the dead reckoning sensors such as the pitch rate sensor 30 and the acceleration sensor 31. In one example, the position sensor 33 may be a GPS sensor and the dead reckoning sensors may be a pitch rate sensor 30 and an acceleration sensor 31 combined to form an IMU. The position sensing system 32 may determine at stage 43 the position of machine 10 based upon the position signals or data received from the GPS sensor. The position as determined by the position sensing system 32 based upon position signals from the position sensor 33 may be referred to as a sensed position of the machine 10 as it is based upon data from the position sensor. The accuracy verification system 38 may be used to confirm or verify the accuracy of the sensed position.

The accuracy verification system 38 may set or store at stage 44 a first initialization position which is equal to the sensed position of the machine 10. The first initialization position is used as a baseline or starting point for the first verification cycle. At stage 45, the position sensing system 32 continues to receive position signals or data from the position sensor 33 and also receives pitch rate signals from the pitch rate sensor 30 and acceleration signals from the acceleration sensor 31. At stage 46, the position sensing system 32 may determine the sensed position of the machine 10 based upon the position signals from the position sensor 33.

In some instances, it may be desirable to utilize a delay or initialization period during which time the accuracy verification system 38 does not compare the sensed position to the calculated position. In other words, the verification cycle does not begin until the passage of a predetermined period of time. The initialization period may be a length of time after the first initialization position is set or an amount of distance machine 10 must move before the dead reckoning process beings. Use of an initialization period for each verification cycle may improve the performance of the accuracy verification system 38. If the initialization period has not expired or passed at decision stage 47, the accuracy verification system 38 may continue in a loop by receiving data from the sensors at stage 45 and determining the sensed position of the machine 10 at stage 46 until the initialization period has passed.

Once the initialization period has expired, the accuracy verification system 38 may determine at stage 50 a first calculated machine position based at least in part upon the first initialization position and the plurality of dead reckoning signals. In doing so, the accuracy verification system 38 begins at the first initialization position and integrates the results from the dead reckoning sensors (e.g., the pitch rate sensor 30 and the acceleration sensor 31) as a dead reckoning system to determine the first calculated position of the machine 10. In other words, the accuracy verification system 38 may utilize a dead reckoning process from the first initialization position to determine the first calculated position of the machine 10. In one example, the pitch rate as determined by the controller 36 based upon the pitch rate signals from the pitch rate sensor 30 and the acceleration as determined by the controller 36 based upon the acceleration signals from the acceleration sensor 31 may be integrated to determine the distance the machine has moved relative to the first initialization position. This distance may be used with the first initialization position to determine the first calculated position of machine 10.

At stage 51, the accuracy verification system 38 may compare the first calculated position determined at stage 50 to the sensed position determined at stage 46. At decision stage 52, the accuracy verification system 38 may determine whether the difference between the sensed position and the first calculated position exceeds the error threshold. In doing so, the accuracy verification system 38 may determine the absolute value of the difference the between the sensed position and the first calculated position and then compare that absolute value to the error threshold.

If the error threshold is exceeded at decision stage 52, an error signal may be generated at stage 53. The error signal may result in the issuance of an alert notification to an operator, an alert notification logged by control system 35, a reduction in the speed or stoppage of the machine 10, and/or any other actions that may be desired. If the absolute value of the difference between the sensed position and the calculated position does not exceed the error threshold at decision stage 52, the accuracy verification system may, at decision stage 54, determine whether the first dead reckoning cycle has been completed. If the first dead reckoning cycle has not been completed, the accuracy verification system 38 continues to receive data from the sensors at stage 45, determines the sensed position of the machine 10 at stage 46, determines the first calculated position at stage 50, compares the first calculated position to the sensed position at stage 51, and determines whether the error threshold has been exceeded at decision stage 52.

If the first dead reckoning cycle has been completed at decision stage 54, the accuracy verification system 38 may begin a new verification cycle by setting a new first initialization position at stage 44 from which the next first dead reckoning cycle will originate and then repeating stages 45-54.

While the first verification cycle set forth in stages 44-54 is operating, a second verification cycle may also be operating in parallel but with the timing offset from that of the first verification cycle. More specifically, at decision stage 61, the accuracy verification system 38 may determine whether an initial overlap period has been completed. Since the first verification cycle and the second verification cycle are offset from each other, the beginning of the initial second verification cycle is delayed to establish the offset between the first verification cycle and the second verification cycle. When the accuracy verification system 38 utilizes two verification cycles, the initial overlap period may be one half of the error detection period. In an embodiment in which the accuracy verification system 38 includes more than two verification cycles with evenly staggered initialization periods (so that each verification cycle is offset from and overlaps with each of the other verification cycles), the offset between each of the verification cycles may be set as 1/n, where n equals the number of staggered, parallel verification cycles.

If the initial overlap period has not been completed at stage 60, the accuracy verification system 38 may continue in a loop at decision stage 60 to delay the beginning of the second verification cycle. Once the initial overlap period has been completed, the second verification cycle may begin at stage 61. The process of the second verification cycle may be substantially identical to the first verification cycle described in stages 44-54 but with the timing staggered from stages 44-54. More specifically, at stage 61, a second initialization position may be set which is equal to the sensed position of the machine 10. The second initialization position is used as the baseline or starting point for the second verification cycle. At stage 45, the position sensing system 32 receives position signals or data from the position sensor 33 and also receives pitch rate signals from the pitch rate sensor 30 and acceleration signals from the acceleration sensors 31. At stage 46, the position sensing system 32 may determine the sensed position of the machine 10 based upon the position signals from the position sensor 33.

A delay or initialization period may be used at decision stage 67 during which time the accuracy verification system 38 does not compare the sensed position to the calculated position. If the initialization period has not expired or passed at decision stage 62, the accuracy verification system 38 may continue in a loop by receiving data from the sensors at stage 45 and determining the sensed position of the machine 10 at stage 46 until the initialization period has passed.

Once the initialization period has expired, the accuracy verification system 38 may determine at stage 70 a second calculated machine position based at least in part upon the second initialization position and the plurality of dead reckoning signals. In doing so, the accuracy verification system 38 begins at the second initialization position and integrates the results from the dead reckoning sensors (e.g., the pitch rate sensor 30 and the acceleration sensor 31) to determine a calculated position of the machine 10. The accuracy verification system 38 may utilize a dead reckoning process from the second initialization position to determine the second calculated position of the machine 10. In one example, the pitch rate as determined by the controller 36 based upon the pitch rate signals from the pitch rate sensor 30 and the acceleration as determined by the controller 36 based upon the acceleration signals from the acceleration sensor 31 may be integrated to determine the distance the machine 10 has moved relative to the second initialization position. This distance may be used with the second initialization position to determine the second calculated position of machine 10.

At stage 71, the accuracy verification system 38 may compare the second calculated position determined at stage 70 to the sensed position determined at stage 46. At decision stage 72, the accuracy verification system 38 may determine whether the difference between the sensed position and the second calculated position exceeds the error threshold. In doing so, the accuracy verification system 38 may determine the absolute value of the difference the between the sensed position and the second calculated position and then compare that absolute value to the error threshold.

If the error threshold is exceeded at decision stage 72, an error signal may be generated at stage 73. The error signal may result in the issuance of an alert notification to an operator, an alert notification logged by control system 35, a reduction in the speed or stoppage of the machine 10, and/or any other actions that may be desired. If the difference between the sensed position and the calculated position does not exceed the error threshold at decision stage 72, the accuracy verification system may, at decision stage 74, determine whether the second dead reckoning cycle has been completed. If the second dead reckoning cycle has not been completed, the accuracy verification system 38 continues to receive data from the sensors at stage 45, determines the sensed position of the machine 10 at stage 46, determines the second calculated position at stage 70, compares the second calculated position to the sensed position at stage 71, and determines whether the error threshold has been exceeded at decision stage 72.

If the second dead reckoning cycle has been completed at decision stage 74, the accuracy verification system 38 may begin a new verification cycle by setting a new second initialization position at stage 61 from which the next second dead reckoning cycle originates and then repeating stages 45, 46, 61, 67, and 70-74.

Referring to FIG. 4, a graph depicts a simulation of the error of the sensed machine position 81 as a function of time as determined by position sensing system 32 based upon data from the position sensor 33. More specifically, displacement of sensed machine position 81 along the y-axis (i.e., relative to the horizontal axis 82) depicts the error of the position sensing system 32. In other words, the difference between the sensed machine position 81 and the horizontal axis 82 depicts the error between the actual machine position and the sensed position of machine 10 as reflected by the position sensing system 32. In one example, sensed machine position 81 may be the position of the machine 10 based upon data from a GPS sensor. The error threshold is depicted as dashed line 112 in FIG. 4 (as well as FIGS. 5-6) for illustrative purposes.

FIG. 5 depicts a graph of simulations of a set of first dead reckoning cycles 90 estimating the position of machine 10 based upon dead reckoning of the machine. The first dead reckoning cycles 90 are continuously repeated but only two full cycles are depicted in FIG. 5. As depicted, a first simulation 91 of a first dead reckoning cycle 90 begins at a first example of a first initialization position 92 that corresponds to the sensed machine position 81 of FIG. 4 at the same time (i.e., at the same location along the horizontal axis 82). In other words, the first example of the first initialization position 92 corresponds (along both the x and y axes) to the position 83 of sensed machine position 81 of FIG. 4. Again, displacement of first simulation 91 along the y-axis (i.e., relative to the horizontal axis 82) depicts the error of the first dead reckoning cycle relative to the actual position of the machine. Error may arise due to the integration of noise and non-constant bias of the dead reckoning sensors during the dead reckoning process and due to errors with respect to the first initialization position 92. Since the first simulation 91 began with the first example of the first initialization position 92 on the horizontal axis 82, the only error in first simulation 91 is that due to the error of the dead reckoning cycle. The first simulation 91 continues until reaching the end 93 of the first simulation 91 of the first dead reckoning cycle 90.

Upon the first simulation 91 of a first dead reckoning cycle 90 ending, a second simulation 94 of a first dead reckoning cycle 90 begins. The second simulation begins at a second example of the first initialization position 95. The second example of the first initialization position 95 corresponds to the position 84 of sensed machine position 81 of FIG. 4. Since position 84 of sensed machine position 81 is displaced from or above the horizontal axis 82 in FIG. 4, the second example of the first initialization position 95 is displaced above the horizontal axis 82 by a like amount in FIG. 5. The second simulation 94 of a first dead reckoning cycle 90 continues until reaching end 96 of that dead reckoning cycle. It should be noted that the error associated with each dead reckoning cycle may be different (as reflected by the different shapes of first simulation 91 and second simulation 94) since the dead reckoning process includes integrating noise and non-constant bias of the dead reckoning sensors. Second simulation 94 began at the second example of the first initialization position 95, which was displaced from the horizontal axis 82, so the error in the second simulation includes both that of the second example of the first initialization position 95 and the error due to the dead reckoning cycle.

FIG. 6 depicts a second graph of simulations of a set of second dead reckoning cycles 100 estimating the position of machine 10 based upon a dead reckoning process of the machine. Second dead reckoning cycles 100 are similar to the first dead reckoning cycles 90 but are offset or staggered by half of the error detection period as may be seen by comparing FIG. 5 to FIG. 6. The second dead reckoning cycles 100 are continuously repeated and one and one half cycles are depicted in FIG. 5.

As depicted, a first simulation 101 of a second dead reckoning cycle 100 begins at a second initialization position 102 that corresponds to the sensed machine position 81 of FIG. 4 at the same time (i.e., the same location along the horizontal axis 82). Second initialization position 102 corresponds (along both the x and y axes) to the position 85 of sensed machine position 81 of FIG. 4. As with FIG. 5, displacement of first simulation 101 along the y-axis (i.e., relative to the horizontal axis 82) depicts the error of the second dead reckoning cycle relative to the actual position of the machine. The error may arise due to the integration of noise and non-constant bias of the dead reckoning sensors during the dead reckoning process and due to errors with respect to the second initialization position 102. Since the first simulation 101 began with the second initialization position 102 on the horizontal axis 82, the only error in first simulation 101 is that due to the error of the dead reckoning cycle. The first simulation 101 continues until reaching the end 103 of the first simulation 101 of the second dead reckoning cycle 100.

Upon the first simulation 101 of the second dead reckoning cycle 100 ending, a second simulation 104 of the second dead reckoning cycle 100 begins. The second simulation 104 begins at a second example of a second initialization position 105. The second example of the second initialization position 105 corresponds to the position 86 of sensed machine position 81 of FIG. 4. Since position 86 of sensed machine position 81 is displaced above the horizontal axis 82 in FIG. 4, the second example of the second initialization position 105 is displaced above the horizontal axis 82 by a like amount in FIG. 6. The second simulation 104 of the second dead reckoning cycle 100 continues until reaching the end (not shown) of that dead reckoning cycle.

It should be noted that the although the integration calculations of the dead reckoning processes of FIGS. 5-6 are different, the dead reckoning signals or data used for each of the first dead reckoning cycles 90 and the second dead reckoning cycles 100 may be the same. In other words, the accuracy verification system 38 may utilize a single set of dead reckoning sensors that generate a single set of data. The data from the dead reckoning sensors may be used for both calculations during the first dead reckoning cycles 90 and the second dead reckoning cycles 100.

FIG. 7 depicts a graph of the difference between the sensed machine position 81 and each of the first dead reckoning cycles 90 and the second dead reckoning cycles 100, respectively. By subtracting the sensed machine position 81 from the first dead reckoning cycles 90 and the second dead reckoning cycles 100, a plurality of overlapping verification cycles 110 may be generated. First verification cycle 111 begins at position 120 aligned with first initialization position 92 on horizontal axis 82 and follows the shape of first simulation 91 of first dead reckoning cycle 90. It may be seen that the first verification cycle 111 does not reach the error threshold (depicted as dashed line 112) before the end 93 of the first simulation 91 of the first dead reckoning cycle 90.

Second verification cycle 113 begins at position 121 aligned with second initialization position 102 on horizontal axis 82 and follows the shape of first simulation 101 of the second dead reckoning cycle 100. Second verification cycle 113 reaches the error threshold 112 at intersection 114 and controller 36 may generate an error signal based upon such intersection. It should be noted that the first verification cycle 111 and the second verification cycle 113 overlap in time (i.e. horizontally) so that even if the second verification cycle is not utilized during an initialization period 115 immediately after beginning the second verification cycle, the accuracy verification system 38 may rely upon the first verification cycle to confirm the accuracy of the sensed machine position 81.

Although the controller 36 may stop the machine 10 upon the generation of an error signal, additional verification cycles are depicted in FIGS. 4-7 for illustrative purposes. Third verification cycle 116 begins at position 122 aligned with first initialization position 95 on horizontal axis 82 and follows the shape of second simulation 94 of first dead reckoning cycle 90. It may be seen that the third verification cycle 116 almost reaches the error threshold 112 at a position 123 generally aligned with position 86 of sensed machine position 81. Fourth verification cycle 117 begins at position 124 aligned with second initialization position 95 on horizontal axis 82 and follows the shape of second simulation 94 of second dead reckoning cycle 100.

As best seen in FIG. 7, each verification cycle 110 overlaps in time (i.e., horizontally) with another verification cycle. As a result, one verification cycle is partway through its cycle when another cycle is starting. If desired, three or more verification cycles 110 may operate in a parallel but staggered or offset manner. The process for additional cycles may be generally identical to the process for the first two staggered cycles but with each additional cycle offset from the others. In an example in which three or more verification cycles 110 overlap, at least two verification cycles will be partway through their cycles each time a new verification cycle begins. This may increase the precision of the accuracy verification system 38.

INDUSTRIAL APPLICABILITY

The industrial applicability of the system described herein will be readily appreciated from the forgoing discussion. The foregoing discussion is applicable to machines 10 that use position sensing systems 32 such as a global navigation satellite system or global positioning system to determine the position of the machine 10. The accuracy verification system 38 may be used at a mining site, a landfill, a quarry, a construction site, a roadwork site, a forest, a farm, or any other area in which it is desired to determine the position of the machine 10.

As machine 10 moves, the controller 36 may receive signals or data from various systems and sensors positioned remote from the machine. A position sensing system 32 may determine a sensed position of the machine 10 within work site 200. Errors in the sensed position may result in the machine 10 being incorrectly positioned within electronic maps of the work site 200 which may in turn result in the machine being positioned in undesirable or dangerous locations.

Relatively large changes in position may be readily identified by controller 36 based upon the sensed locations and the operating conditions of machine 10. However, gradual errors or changes in position may be more difficult to identify. Accuracy verification system 38 may be used to confirm the accuracy or integrity of the sensed position of the machine 10. The accuracy verification system 38 may be configured to utilize position sensing system 32 together with signals from dead reckoning sensors that sense movement of the machine 10 to check or determine the accuracy of the sensed position.

Dead reckoning is typically used to determine the position of the machine 10 during the interval between the receipt of signals used to determine the sensed position. However, as disclosed herein, the accuracy verification system 38 may be configured to operate a plurality of staggered or offset, parallel dead reckoning cycles while the position sensing system 32 is receiving signals from position sensor 33. More specifically, the accuracy verification system 38 may be configured to periodically set a baseline or initialization position (such as first initialization position 92 and second initialization position 102) based upon the sensed position of the machine 10. The signals from the dead reckoning sensors may then be used with the initialization position as part of a dead reckoning cycle to determine a calculated position of the machine 10. The calculated position and the sensed position may be compared and if difference between the calculated position and the sensed position is greater than the error threshold, the controller 36 may generate an error signal which may result in a reduction in speed or stoppage of the machine, and/or any other desired action.

It will be appreciated that the foregoing description provides examples of the disclosed system and technique. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for determining an error in a sensed position of a machine, comprising:
a position sensing system, including a GPS sensor, mounted on the machine for determining a sensed position of the machine;
a dead reckoning system, including an inertial measurement unit, mounted on the machine for determining a calculated position of the machine; and
a controller configured to:
store an error threshold defining a maximum acceptable distance between the sensed position of the machine and the calculated position of the machine;
execute a first verification cycle configured to:
determine an initialization position based upon the position sensing system;
determine a calculated position based upon the initialization position and the dead reckoning system;

determine a sensed position based upon the position sensing system;

determine a difference between the calculated position and the sensed position;

compare the difference to the error threshold; and generate an error signal if the difference exceeds the error threshold;

execute a second verification cycle configured to:

determine a second initialization position of the machine based upon the position sensing system, the second initialization position being spaced from the initialization position, determine a second calculated position based upon the second initialization position and the dead reckoning system, determine a second difference between the second calculated position and the sensed position, compare the second difference to the error threshold; and generate an error signal if the second difference exceeds the error threshold;

wherein the first and second initialization positions are staggered such that the second verification cycle starts before the first verification cycle is completed.

2. The system of claim 1, wherein the inertial measurement unit includes an acceleration sensor, the acceleration sensor being configured to provide an acceleration signal indicative of an acceleration of the machine, and the controller is further configured to receive an acceleration signal from the acceleration sensor and determine the calculated position based upon the acceleration signal.

3. The system of claim 2, wherein the inertial measurement unit further includes a pitch rate sensor mounted on the machine, the pitch rate sensor being configured to provide a pitch rate signal indicative of a pitch rate of the machine, and the controller is further configured to receive a pitch rate signal from the pitch rate sensor and determine the calculated position based upon the pitch rate signal.

4. The system of claim 1, wherein the inertial measurement unit includes a pitch rate sensor, the pitch rate sensor being configured to provide a pitch rate signal indicative of a pitch rate of the machine, and the controller is further configured to receive a pitch rate signal from the pitch rate sensor and determine the calculated position based upon the pitch rate signal.

5. The system of claim 1, wherein the controller is further configured to stop the machine upon generating an error signal.

6. The system of claim 1, wherein the controller is further configured to slow the machine upon generating an error signal.

7. The system of claim 1, wherein the controller is further configured to delay determining the difference until passage of a predetermined period of time after determining the initialization position.

8. A controller-implemented method for determining an error in a sensed position of a machine, comprising:

storing an error threshold defining a maximum acceptable distance between a sensed position of the machine based upon a position sensing system including a GPS sensor and a calculated position of the machine based upon a dead reckoning system including an inertial measurement unit which further includes a pitch rate sensor and an acceleration sensor;

executing a first verification cycle comprising:

determining an initialization position based upon the position sensing system;

determining a calculated position based upon the initialization position and the dead reckoning system;

determining a sensed position based upon the position sensing system;

determining a difference between the calculated position and the sensed position;

comparing the difference to the error threshold; and generating an error signal if the difference exceeds the error threshold;

executing a second verification cycle comprising:

determining a second initialization position of the machine based upon the position sensing system, the second initialization position being spaced from the initialization position;

determining a second calculated position based upon the second initialization position and the dead reckoning system;

determining a second difference between the second calculated position and the sensed position;

comparing the second difference to the error threshold; and generating an error signal if the second difference exceeds the error threshold;

wherein the first and second initialization positions are staggered such that the second verification cycle starts before the first verification cycle is completed.

9. The method of claim 8, further including providing an acceleration signal from the acceleration sensor indicative of an acceleration of the machine, and determining the calculated position based upon the acceleration signal.

10. The method of claim 9, further including providing a pitch rate signal from the pitch rate sensor indicative of a pitch rate of the machine, and determining the calculated position based upon the pitch rate signal.

11. The method of claim 8, further including providing a pitch rate signal from the pitch rate sensor indicative of a pitch rate of the machine, and determining the calculated position based upon the pitch rate signal.

12. The method of claim 8, further including stopping the machine upon generating an error signal.

13. The method of claim 8, further including slowing the machine upon generating an error signal.

14. The method of claim 8, further including delaying determining the difference until passage of a predetermined period of time after determining the initialization position.

15. An autonomously operated machine comprising:

a propulsion system;

a steering system;

a position sensing system including a GPS sensor mounted on the machine for determining a sensed position of the machine;

a dead reckoning system including an inertial measurement unit, mounted on the machine for determining a calculated position of the machine;

an accuracy verification system for determining an error in the sensed position; and a controller configured to:

store an error threshold defining a maximum acceptable distance between the sensed position of the machine and the calculated position of the machine;

execute a first verification cycle configured to:

determine an initialization position based upon the position sensing system;

determine a calculated position based upon the initialization position and the dead reckoning system;

determine a sensed position based upon the position sensing system;
determine a difference between the calculated position and the sensed position;
compare the difference to the error threshold; and
generate an error signal if the difference exceeds the error threshold;
execute a second verification cycle configured to:
determine a second initialization position of the machine based upon the position sensing system, the second initialization position being spaced from the initialization position;
determine a second calculated position based upon the second initialization position and the dead reckoning system;
determine a second difference between the second calculated position and the sensed position, compare the second difference to the error threshold; and
generate an error signal if the second difference exceeds the error threshold;
wherein the first and second initialization positions are staggered such that the second verification cycle starts before the first verification cycle is completed.

* * * * *